(12) United States Patent
Northcott et al.

(10) Patent No.: US 7,869,627 B2
(45) Date of Patent: *Jan. 11, 2011

(54) POST PROCESSING OF IRIS IMAGES TO INCREASE IMAGE QUALITY

(75) Inventors: Malcolm J. Northcott, Felton, CA (US); J. Elon Graves, Los Gatos, CA (US)

(73) Assignee: AOptix Technologies, Inc., Campbell, CA (US)

( * ) Notice: Subject to any disclaimer, the term of this patent is extended or adjusted under 35 U.S.C. 154(b) by 735 days.

This patent is subject to a terminal disclaimer.

(21) Appl. No.: 11/752,899

(22) Filed: May 23, 2007

(65) Prior Publication Data

US 2007/0216798 A1    Sep. 20, 2007

Related U.S. Application Data

(63) Continuation-in-part of application No. 11/297,578, filed on Dec. 7, 2005, now Pat. No. 7,428,320.

(60) Provisional application No. 60/803,006, filed on May 23, 2006, provisional application No. 60/654,638, filed on Feb. 17, 2005, provisional application No. 60/634,331, filed on Dec. 7, 2004.

(51) Int. Cl.
*G06K 9/46* (2006.01)
*G01C 3/12* (2006.01)
*A61B 3/10* (2006.01)

(52) U.S. Cl. .................... 382/117; 382/190; 351/221; 356/71

(58) Field of Classification Search ................ 382/117, 382/100, 115, 181, 190, 276, 293, 128; 348/E5.03, 348/207.99, 143, 35, 36, E5.038, E7.085, 348/576; 359/368, 362, 363; 356/456, 71, 356/2, 450; 351/206, 200, 221, 207, 205, 351/211, 212, 220; 606/2, 4; 430/311

See application file for complete search history.

(56) References Cited

U.S. PATENT DOCUMENTS

| 4,106,856 A | 8/1978 | Babish |
| 5,214,455 A | 5/1993 | Penney et al. |
| 5,956,122 A | 9/1999 | Doster |

(Continued)

OTHER PUBLICATIONS

B. Roy Freiden, *Restoring with Maximum Likelihood and Maximum Entropy*, Journal of the Optical Society of America, Apr. 1972, pp. 511-518, vol. 62, No. 4.

(Continued)

*Primary Examiner*—Sheela C Chawan
(74) *Attorney, Agent, or Firm*—Fenwick & West LLP

(57) ABSTRACT

A rapid iris acquisition, tracking, and imaging system can be used at longer standoff distances and over larger capture volumes, without the active cooperation of subjects. Light illuminates the subjects' eyes and a high resolution camera captures images of the irises. The images of the irises are processed by a post processing module to improve their quality. In one approach, the point spread function of the image capture subsystem is estimated using glint reflections from the eye, and the estimated point spread function is used in deconvolution to increase the resolution of the iris images. The post processed iris images have sufficient resolution to be used for biometric identification.

108 Claims, 5 Drawing Sheets

U.S. PATENT DOCUMENTS

| | | | |
|---|---|---|---|
| 6,059,773 | A | 5/2000 | Maloney et al. |
| 6,095,651 | A | 8/2000 | Williams et al. |
| 6,099,522 | A | 8/2000 | Knopp et al. |
| 6,200,266 | B1 * | 3/2001 | Shokrollahi et al. ......... 600/438 |
| 6,252,977 | B1 | 6/2001 | Salganicoff et al. |
| 6,333,988 | B1 | 12/2001 | Seal et al. |
| 6,439,720 | B1 | 8/2002 | Graves et al. |
| 6,447,119 | B1 | 9/2002 | Stewart et al. |
| 6,452,145 | B1 | 9/2002 | Graves et al. |
| 6,464,364 | B2 | 10/2002 | Graves et al. |
| 6,568,647 | B2 | 5/2003 | Graves et al. |
| 6,609,794 | B2 | 8/2003 | Levine |
| 6,714,665 | B1 | 3/2004 | Hanna et al. |
| 6,721,510 | B2 | 4/2004 | Graves et al. |
| 6,922,250 | B2 | 7/2005 | Fercher |
| 7,148,970 | B2 * | 12/2006 | de Boer ..................... 356/497 |
| 7,199,767 | B2 * | 4/2007 | Spero ............................ 345/7 |
| 7,226,166 | B2 | 6/2007 | Della Vecchia et al. |
| 7,280,676 | B2 | 10/2007 | Miura et al. |
| 7,391,887 | B2 * | 6/2008 | Durnell ..................... 382/117 |
| 7,428,320 | B2 * | 9/2008 | Northcott et al. ........... 382/117 |
| 7,652,685 | B2 | 1/2010 | Wach et al. |
| 2003/0025877 | A1 | 2/2003 | Yancey et al. |
| 2003/0169334 | A1 | 9/2003 | Braithwaite et al. |
| 2003/0226978 | A1 | 12/2003 | Ribi et al. |
| 2004/0165147 | A1 | 8/2004 | Della Vecchia et al. |
| 2005/0204329 | A1 * | 9/2005 | Pauca et al. ................... 716/21 |
| 2006/0092376 | A1 | 5/2006 | Baek et al. |

OTHER PUBLICATIONS

S.F. Gull et al., *Image reconstruction from incomplete and noisy data*, Nature, Apr. 20, 1978, pp. 686-690, vol. 272.

J.A. Hogbom, *Aperture synthesis with a non-regular distribution of interferometer baselines*, Astronomy and Astrophysics Supplement, 1974, pp. 417-426, vol. 15.

International Search Report and Written Opinion for PCT/US05/44313, Oct. 16, 2006, 9 pages.

Peter A. Janson, *Method for Determining the Response Function of a High-Resolution Infrared Spectrometer*, Journal of the Optical Society of America, Feb. 1970, pp. 184-191, vol. 60, No. 2.

Stuart M. Jefferies et al., *Restoration of Astronomical Images by Iterative Blind Deconvolution*, The Astrophysical Journal, Oct. 1, 1993, pp. 862-874, vol. 415.

William H. Press et al., *Numerical Recipes: The Art of Scientific Computing*, 1986, pp. 417-420 & 495-497, University Press, U.S.A.

Niels Zagers, *Foveal Reflection Analyser on the Spectral and Directional Reflectance of the Retina*, Jan. 27, 2004, pp. 1-132, Ponsen & Looijen BV, Wageningen, The Netherlands.

Office Action for U.S. Appl. No. 12/192,785, Apr. 29, 2009, 7 Pages.

European Patent Office Extended European Search Report, Patent Application No. EP 05853275.5 Feb. 1, 2010, six pages.

European Patent Office Communication, Patent Application No. EP 05853275.5 May 17, 2010, one page.

*HBOX™ Specifications*, 2007, [Online], Retrieved from the InternetURL:<www.hoyosgroup.com>.

*HIIDE Series 4*, [online], 2 pages, retrieved on Apr. 23, 2008, retrieved from the Internet, URL:<http://www.securimetrics.com/solutions/hiide_specs.htm>.

*Iris & Retina Multi- Modal System*, [online], 1 page, retrieved from the Internet, URL:<http://retica.com/site/technology/irisretina.htm>.

*IRIS on the Move™ Portal System Specifications*, Brochure, 2007, 1 page.

*IRIS on the Move™ Flexible Design Platform - Multiple Configurations*, Brochure, 2007, 1 page.

*Pier 2.3*, [online], 2 pages, retrieved on Apr. 23, 2008, retrieved from the Internet, URL:<http://www.securimetrics.com/solutions/pier_specs.html>.

United States Office Action, U.S. Appl. No. 12/021,189, Jun. 23, 2010, fifteen pages.

* cited by examiner

POST PROCESSING OF IRIS IMAGES TO INCREASE IMAGE QUALITY

CROSS-REFERENCE TO RELATED APPLICATION(S)

This application claims priority under 35 U.S.C. § 119(e) to U.S. Provisional Patent Application Ser. No. 60/803,006, filed May 23, 2006, which is a continuation-in-part of U.S. patent application Ser. No. 11/297,578, filed on Dec. 7, 2005, entitled "Iris Imaging Using Reflection From The Eye," which claims priority under 35 U.S.C. §119(e) to both U.S. Provisional Patent Application Ser. No. 60/654,638, "Biometric Identification and Iris Imaging Using Retinal Retro-Reflection," filed Feb. 17, 2005, and U.S. Provisional Patent Application Ser. No. 60/634,331, "Adaptive Optics (AO) Imaging Applied to Biometric Identification Using Iris Imaging," filed Dec. 7, 2004. The subject matter of all of the foregoing is incorporated herein by reference in their entirety.

BACKGROUND OF THE INVENTION

1. Field of the Invention

This invention relates to imaging of the human iris, as may be used for biometric identification. More specifically, this invention relates to post processing of images of the human iris, as may be used to increase the quality of these images.

2. Description of the Related Art

As traditional forms of personal identification become vulnerable to advancing technology, biometric identification is increasingly seen as a viable approach to personal identification. Techniques such as voice recognition, fingerprinting, and iris imaging rely on physical personal traits that are difficult to change or duplicate.

However, biometric identification via iris imaging typically requires a high resolution image of the iris in order to resolve the fine details necessary to make a positive identification. An image of an iris with approximately 200 micron or better spatial resolution typically is required to uniquely distinguish the fine muscle structure of human irises, as may be required for identification purposes. In systems where the subject is actively cooperating, conditions such as illumination geometry, camera resolution, exposure time, and wavelength of light can be optimized in order to capture a high contrast and high resolution image of the fine structure of the iris. However, the situation becomes significantly worse when the subject is not actively cooperating.

The "capture volume" of an iris imaging system is the volume over which the iris imaging system can capture iris images of sufficiently high resolution. Traditional systems have a small capture volume—so small as to make traditional iris imaging systems unsuitable for use in uncooperative situations, such as iris imaging over large groups of people, over longer standoff distances, or for covert identification applications. For example, it may be desirable to capture iris images of subjects as they walk through a portal, such as a metal detector, or in places like airports, train stations, border crossings, secure building entrances and the like.

However, the high resolution and longer standoff requirements in these applications place significant challenges on iris imaging systems. For example, a short standoff system using commercial CCD technology (e.g., 5 megapixels) could have a field of view of approximately 15 cm at a 1 m standoff range, yielding a spatial resolution of approximately 75 microns per pixel at the 1 m standoff range. This resolution is sufficient for biometric identification. However, a 1 m standoff range typically will require the subject's active cooperation to position their head in the field of view and at the correct focus distance.

If the standoff range is increased to 10 m for example, the situation becomes significantly more difficult. If the same camera were used at a standoff of 10 m, maintaining the same angular resolution would result in a spatial resolution of 750 µm per pixel, which is not sufficient for biometric identification. The imaging optics could be designed to yield a spatial resolution of 75 µm per pixel, but this would then result in a 15 cm wide field of view at 10 m. Keeping the iris within this field of view is difficult. The field of view could be increased while maintaining the same resolution by increasing the number of pixels in the camera, but this increases the cost and complexity of the camera.

Therefore, there is a need for iris imaging systems capable of generating sufficiently high resolution and high quality iris images, and at longer standoff distances and with sufficiently large fields of view but without requiring unusually large or complex cameras. These systems could be used to enable iris imaging over increased capture volumes and/or at longer standoff distances.

SUMMARY OF THE INVENTION

Embodiments of the present invention include iris imaging systems that use post-processing to increase the quality of captured iris images, such as resolution, contrast or noise characteristics. In one aspect, an iris imaging system captures lower resolution images and an image post processing module increases the resolution of the images. As a result, the iris imaging system can be used at longer standoff distances and/or over larger capture volumes, without the active cooperation of subjects.

In one embodiment, light illuminates the subjects' eyes. Reflection from the eyes (e.g., retro-reflection from the retina or glint reflection from the cornea) is used to steer (and preferably also focus) a camera to the eyes in order to capture images of the irises. The captured iris images are post processed by the imaging system to improve the quality of the images, making them suitable for biometric identification.

In one embodiment, the iris imaging system includes an image capture subsystem and an image post processing module. The image capture subsystem captures images of irises, possibly with resolution that is not sufficient for biometric identification. The image post processing module processes the captured images to generate higher resolution (or otherwise higher quality) images that are sufficient for biometric identification.

In one embodiment, the post processing module estimates the point spread function (PSF) of the image capture subsystem and uses this estimate of the PSF with a deconvolution algorithm to improve the resolution of the captured image. The PSF is a measure of the "blur" introduced by the image capture subsystem, and the post processing module uses an estimate of the PSF to reverse the blurring effect. In one approach, the PSF is estimated by analyzing a reflection from the subject's eye. The same reflection could also be used for other purposes, for example to drive an adaptive optics loop used elsewhere for tracking and/or focusing on the iris.

In another embodiment, the image post processing module uses blind deconvolution techniques to improve the resolution of the captured image. In one implementation, the iris imaging system obtains multiple images of an iris, for example in rapid succession, which it then uses to improve the resolution of a final post-processed image of the iris. If desired, the multiple images of an iris that are obtained from the imaging system can be transformed by the image post processing module using conformal or non-conformal distortion techniques. In general the required mappings will be one to one (bijective). The image post processing module can also use the set of captured images to estimate the PSF, to increase the signal to noise ratio, and/or to create superresolution images.

Turning now to the image capture subsystem, in one embodiment, the image capture subsystem includes a camera, a light source and a fine tracking system. The light source produces light that illuminates eyes within a capture volume. The fine tracking system steers the camera to eyes, based on a reflection from the eyes, preferably either a retro-reflection or a glint reflection. The camera then captures images of the iris, possibly with resolution that is not sufficient for biometric identification (until after post processing).

In one approach, the fine tracking system includes an adaptive optics loop that is driven by the reflected light. For example, the adaptive optics loop can include a deformable mirror, a wavefront sensor and a controller. The wavefront sensor senses the wavefront of the reflected light and a controller drives the deformable mirror based on the sensed wavefront. The deformable mirror corrects the incoming wavefront, thus steering the camera to the eye (i.e., correction of tip and tilt wavefront errors). The deformable mirror may also focus the camera (i.e., correction of focus-error). In this way, the image capture subsystem can acquire iris images, even without the subject's active cooperation.

The iris imaging system may also include an acquisition subsystem that identifies the approximate location of subjects within a capture volume. For example, a wide field of view acquisition subsystem may be coupled with a narrower field of view image capture subsystem. The acquisition subsystem identifies the approximate location of subjects, and the image capture subsystem slews from one subject to the next to acquire images of their irises. A controller coordinates the two subsystems. In one approach, the acquisition subsystem identifies the approximate location of subjects based on retro-reflections from the subjects' eyes. This is convenient since the circular shape of the eye pupil allows one to easily distinguish retro-reflections from the eye from other light sources.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

System Overview

Figure 1:
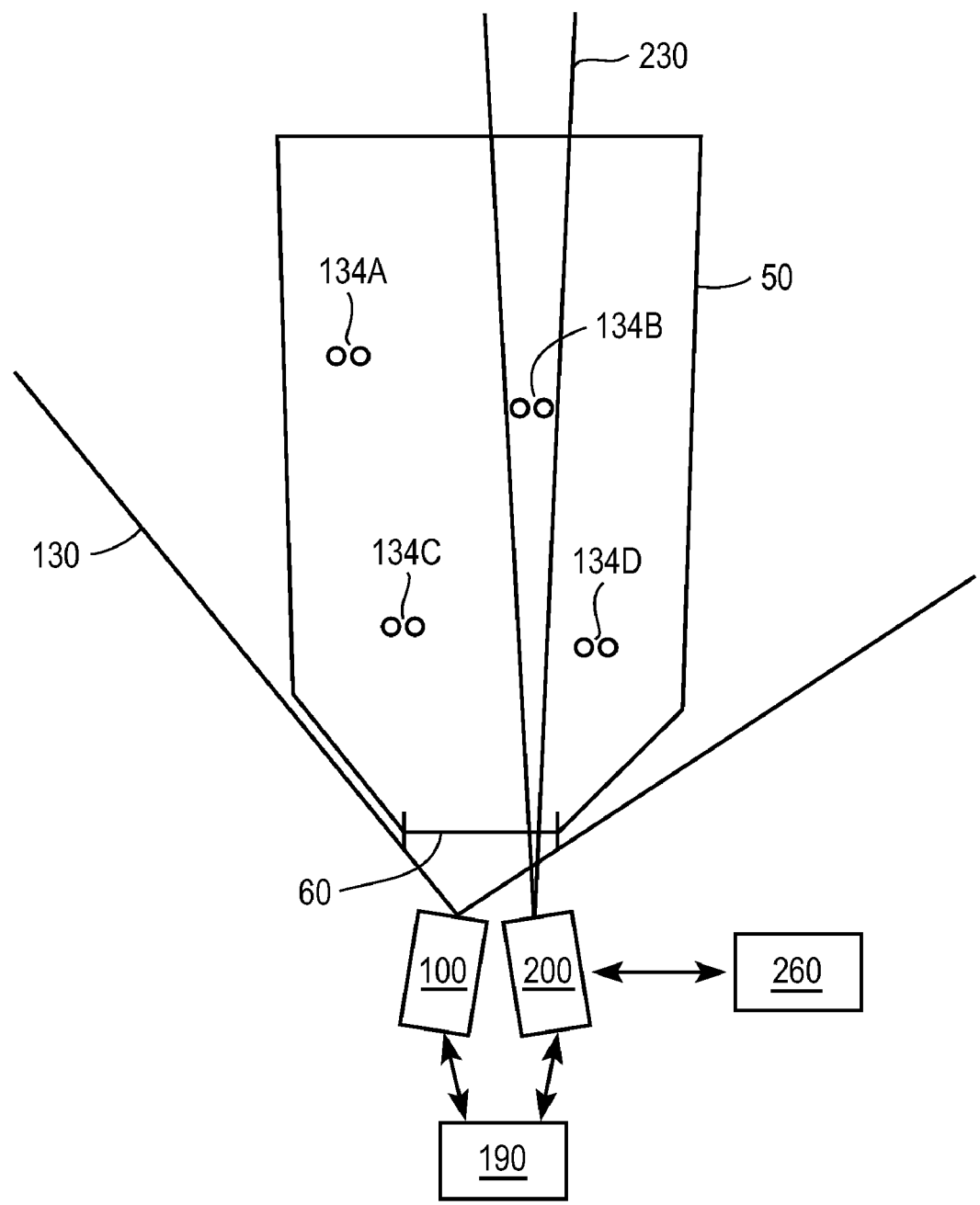
FIG. 1 is an illustration of an iris imaging system according to the present invention.

FIG. 1 is an illustration of an iris imaging system according to the present invention. The iris imaging system includes an image capture subsystem 200, optionally an acquisition subsystem 100, and an image post processing module 260. The system is designed to capture iris images of many eyes 134 over a large capture volume 50, typically without the active cooperation of the subjects. In one application, the subjects are passing through a portal 60 (such as a doorway or metal detector), the capture volume 50 is the entranceway leading up to the portal, and the iris imaging system captures iris images as the subjects pass through the capture volume. In many applications, the capture volume can be defined based on a portal or other bottleneck for the flow of people. Examples include corridors, turnstiles, toll booths, elevator doors, escalators and parking garage entrances. Other examples include checkout lines or other queues, crosswalks, sidewalks and roadways.

This situation typically is "uncooperative," meaning that the subjects are not actively cooperating in the iris imaging. For example, they are not placing their heads into a device to allow capture of iris images. Rather, they are simply walking through the portal and the system captures their iris images as they do so. They may even be unaware that the system is doing so. If stealth is important, the wavelengths should be chosen to be non-visible.

The image capture subsystem 200 captures the iris images for each subject. However, since the image capture subsystem 200 is operating at longer standoff distances, the captured iris images may not have sufficient resolution to allow biometric identification. The captured iris images typically will not be diffraction limited and usually have a relatively poor signal to noise ratio due to illumination constraints for eye safety. The image post processing module 260 can address many of the typical blur problems due to motion and slight defocus. Thus, the resolution of the captured images can be significantly improved by post processing the images, which is the function of the image post processing module 260. The remainder of this disclosure provides further details, first about image capture and later about image post processing.

Image Capture

Referring again to FIG. 1, in order to obtain sufficient resolution, the image capture subsystem 200 typically has a fairly narrow field of view 230. Therefore, in order to cover the entire capture volume, the image capture subsystem 200 is actively steered from one subject to the next. Coarse tracking of subjects can be achieved in many different ways. In FIG. 1, an acquisition subsystem 100 with a wide field of view 130 is used to identify the approximate location of each subject. This information is used to coarsely steer the image capture subsystem 200 to the general vicinity of the subject. Once in the general vicinity, fine tracking is achieved by illuminating the subject's eye with an optical beam and steering the image capture subsystem 200 to the eye based on a reflection from the subject's eye. Examples of eye reflections include retro-reflection from the retina and glint reflection from the corneal surface. The eye reflection can also be used to focus the image capture subsystem 200 on the iris to capture the high resolution image. The tracking (and focus) occurs fairly rapidly in real-time if a large capture volume and throughput of subjects is to be accommodated.

Different devices can be used for the acquisition subsystem 100 and for the image capture subsystem 200. The acquisition subsystem 100 can also be based on tracking subjects using reflection from their eyes. Alternately, it can be based on completely different mechanisms. For example, the acquisition subsystem 100 might capture conventional digital images of the capture volume. Software is then used to identify which parts of each captured image represent humans and/or which part of each human is his face or eyes. Frame to frame comparisons can be used to track movement of subjects. Stereoscopic systems (based on eye reflection, conventional imaging or other approaches) can be used to triangulate subject positions within the capture volume.

In FIG. 1, the acquisition subsystem 100 is shown as a single box with a wide field of view 130. This is merely a representation. The acquisition subsystem 100 is not limited to a single box. In the stereoscopic example, equipment is positioned at different locations in order to capture different viewpoints. Even if a stereoscopic approach is not used, multiple cameras can still be used advantageously, for example to more efficiently cover the entire capture volume 50.

The wide field of view 130 also need not be implemented literally as shown in FIG. 1. Each acquisition camera(s) may have a wide field of view that covers the entire capture volume 50, as shown in FIG. 1. Alternately, each acquisition camera may cover less than the entire capture volume 50, but the cameras together cover the entire capture volume 50. In addition, the cameras may be scanning rather than staring and their instantaneous fields of view may be smaller than the capture volume 50. At any instant in time, only a fraction of the entire capture volume is covered but, over time, the entire capture volume is covered.

As a final example, the acquisition subsystem 100 may not be based on cameras at all. Other types of position sensors or intrusion sensors may be used to determine the location of subjects. For example, the capture volume 50 may be covered by a grid of light beams. The position of subjects is determined by the subjects' breaking the light beams. In a different approach, floor mounted pressure pads may be used to determine subject positions. Sonar, radar, lidar, and thermal detection or imaging are examples of other technologies that can be used to determine subject positions. For certain types of sensors, the term "field of view" may not even be applicable, so long as the acquisition subsystem 100 is sufficient to cover the capture volume 50.

Controller 190 coordinates the two subsystems. The information from the acquisition subsystem 100 is used by the image capture subsystem 200 (via controller 190) to coarsely steer the narrow field of view 230 from subject to subject. As with the acquisition subsystem 100, many different designs for the image capture subsystem 200 are also possible. In one approach, conventional devices such as steering mirrors or gimbals are used to coarsely steer the narrow field of view 230 to the subject 134. An adaptive optics system (not shown in FIG. 1) is then used to achieve fast, fine tracking of the subject 134 and optionally also focus adjustment for the image capture. The adaptive optics system is driven by the eye reflection from the subject's eye 134 and/or by other position and distance measurement techniques. Other approaches can also be used. Risley prisms, liquid crystal phased arrays, real time holograms and Bragg gratings are examples of other steering devices. Other signal sources could include glints, parallax using images or eye reflections, and time of flight lidar.

Figure 2:
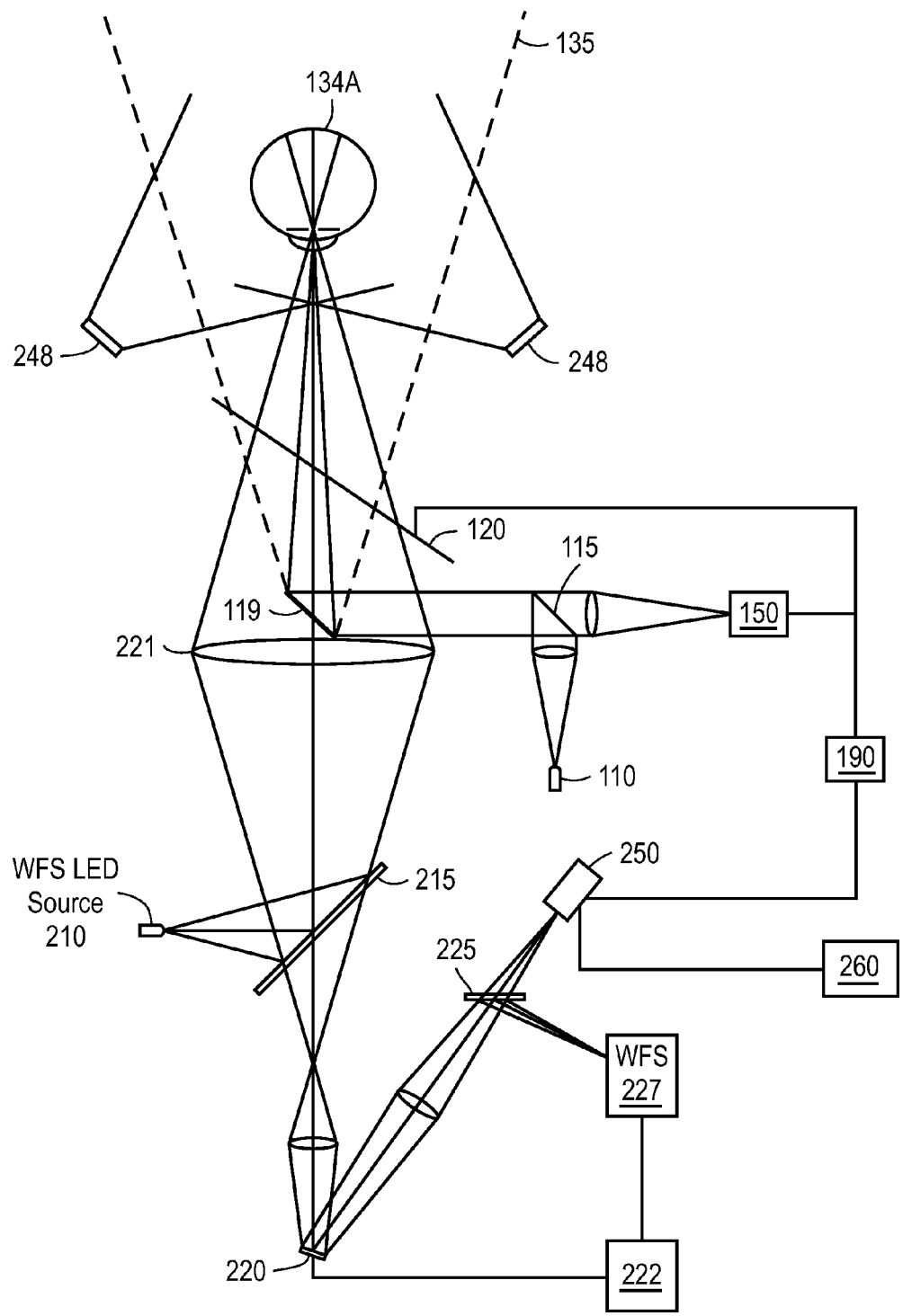
FIG. 2 is an illustration of another iris imaging system according to the present invention, based on retro-reflection from the eye.

FIG. 2 is an illustration of an example iris imaging system according to the present invention, based on retro-reflection from the eye. In this example, the acquisition subsystem 100 includes a light source 110, a beam splitter 115, a small "pickoff" mirror 119 and a camera 150. The image capture subsystem 200 includes a light source 210, a beamsplitter 215, a deformable mirror 220, a beamsplitter 225, a wavefront sensor 227 and a controller 222. It also includes a light source 248 and a camera 250. For convenience, the various light sources may be referred to as the acquisition light source 110, the WFS light source 210 and the iris imaging light source 248, respectively, to distinguish them from each other. The iris imaging system also includes a coarse tip-tilt steering mirror 120 controlled by controller 190, which is used as part of both the acquisition subsystem 100 and the image capture subsystem 200. In FIG. 2, the steering mirror 120 is depicted as a line through the optical beam but, for simplicity, reflection off the steering mirror is not shown (i.e., the optical path is unfolded with respect to steering mirror 120). Various lenses (or other optics) are used to collimate, focus, image or otherwise relay the optical beams throughout the system.

The acquisition subsystem 100 operates as follows. The acquisition light source 110 is the illumination for camera 150. Light produced by light source 110 reflects off beamsplitter 115, and mirror 119. Beamsplitter 115 separates light produced by source 110 that is exiting the system and light returning to the system to be imaged onto camera 150. Beamsplitter 115 could be a polarizing beamsplitter, which together with a quarterwave plate could be used to suppress back reflection and specular reflections. Beamsplitter 115 could also be a neutral beamsplitter (i.e., without polarization selectivity) for low cost and simplicity. Mirror 119 combines the optical paths of the acquisition subsystem 100 and the image capture subsystem 200 so they are generally aligned along a common optical axis. In this example, the two subsystems operate at different wavelengths, so mirror 119 is a dichroic beamsplitter that reflects the wavelengths of the acquisition subsystem 100 and passes the wavelengths of the image capture subsystem 200. The outgoing illumination from light source 110 then reflects off coarse steering mirror 120 to illuminate the acquisition subsystem 100's wider field of view 135. The field of view 135 may stare across the entire capture volume 50 or may be scanned across the capture volume. In this example, the field of view 135 is not wide enough to cover the entire capture volume in a staring mode. Rather, it is scanned across the capture volume by steering mirror 120. Subjects within the field of view 135 are represented by eyes 134, which are illuminated by the acquisition light source 110.

Eyes 134 within the field of view 135 retro-reflect light back to the coarse steering mirror 120, which directs the light to camera 150 via mirror 119 and beamsplitter 115. Camera 150 is a wide angle camera used to identify the general locations of eyes 134. In one implementation, the camera 150 is an electronic image sensor such as a CCD that periodically records discrete images of field of view 135. In one approach, the camera 150 records rapid sequences of images to monitor the movement of objects 134 within the field of view 135. The signals from the wide angle camera are analyzed by software (e.g., contained in controller 190) to identify eyes, which appear as bright circular spots due to the retro-reflections from the eyes 134. The camera 150 operates at the same wavelength as the illuminating source 110. Wavelength filters can be used to reject ambient light on the return optical path, while passing the illuminating wavelength. In addition, the light source 110 can be strobed. Synchronization of the camera 150 exposures with the source 110 strobing can also increase the isolation between imaging and guiding (or wavefront sensor) cameras. Such synchronization can also reduce the effects of background light contamination.

Once eyes 134 are identified, the controller 190 determines a plan for imaging the irises. Preferably, iris images of both eyes are captured (although not necessarily simultaneously), in order to increase the accuracy of identification. In FIG. 2, the iris 134A is being imaged. If necessary, the controller 190 directs the coarse steering mirror 120 to bring the eye of interest 134A within the narrower field of view for the image capture subsystem 200. As drawn in FIG. 2, the coarse steering mirror 120 also steers the wide field of view 135 for the acquisition subsystem 100, although this is not required. One advantage of steering the acquisition subsystem 100 and image capture subsystem 200 together is that a fixed relationship between the wavefront sensor 227 and the acquisition camera 150 is maintained.

The image capture subsystem 200 operates as follows. WFS light source 210 illuminates the eye 134A. Light produced by light source 210 reflects off beamsplitter 215, propagates through lens system 221 and mirror 119, and is directed by steering mirror 120 to the eye 134A. Since this light is coming from the image capture subsystem 200, it has a narrower field of view than the field of view 135 of the acquisition subsystem. A portion of the illuminating light enters the eye 134A, which retro-reflects light back along the same path: steering mirror 120 to lens system 221 to beamsplitter 215. The return light passes through the beamsplitter 215, reflects off deformable mirror 220 and is directed by beamsplitter 225 to the wavefront sensor 227. The wavefront sensor 227, controller 222 and deformable mirror 220 form an adaptive optics loop that is driven based on the retro-reflected light from the eye 134A.

While adaptive optics can be used in many applications to correct for high order aberrations, in this case, the adaptive optics loop is used mainly for fast tracking of the eye 134A (i.e., correction of tip/tilt errors in the wavefront) and preferably also for focus correction. This keeps the iris 134A within the narrow field of view of camera 250 and also focuses the camera (if focus correction is implemented). In this example, the light source 210 does not provide the primary illumination for camera 250. Rather, additional light sources 248 (i.e., the iris imaging light sources) provide off-axis illumination of the irises 134 for camera 250. For example, LEDs in the near infrared wavelength range can be used. The protective pigment melanin is more transparent at longer wavelengths. Thus, the details of the iris structure are more easily seen in heavily pigmented eyes by using light sources of these wavelengths. Alternatively, any other light source could be used that conforms to safety limits. The off-axis illumination generally results in higher contrast and fewer artifacts. Off-axis illumination angle also effects positioning of glints which can be deleterious to the identification accuracy. Glints can also be reduced by using polarized illumination with polarizing filters for the iris camera 250. In alternate approaches, illumination for camera 250 can be provided by ambient lighting, visible or infrared flash, or combinations of these.

Traditional adaptive optics systems, such as those developed for astronomy, may be too large, complex and/or costly to be effectively used in applications such as iris imaging. However, recent advances by AOptix Technologies of Campbell, Calif., have resulted in the development of complete adaptive optics systems, including electronics, that achieve sizes smaller than a shoe box. The AOptix adaptive optics systems require less than 25 W of power and can reliably operate unattended for extended periods of time. The small size, weight and power and high reliability of the AOptix adaptive optics systems make them suitable for applications such as the iris imaging applications described herein.

In these more compact systems, the deformable mirror 220 is a deformable curvature mirror based on applying different voltages across different areas of a piezoelectric material, thus causing deformation. Further details for this type of deformable mirror are described and shown in U.S. Pat. No. 6,464,364, "Deformable Curvature Mirror," filed Jan. 25, 2001 and issued Oct. 15, 2002, by J. Elon Graves and Malcolm J. Northcott; U.S. Pat. No. 6,568,647, "Mounting Apparatus for Deformable Mirror," filed Jan. 25, 2001 and issued May 27, 2003, by J. Elon Graves and Malcolm J. Northcott; and U.S. Pat. No. 6,721,510, "Atmospheric Optical Data Transmission System," filed Jun. 16, 2001 by J. Elon Graves and Malcolm J. Northcott. Furthermore, the wavefront sensor 227 is a wavefront curvature sensor based on defocused pupil images. Further details for this type of wavefront curvature sensor are described and shown in U.S. Pat. No. 6,452,145, "Method and Apparatus for Wavefront Sensing," filed May 26, 2000 and issued Sep. 17, 2002, by J. Elon Graves and Malcolm J. Northcott; and U.S. Pat. No. 6,721,510, "Atmospheric Optical Data Transmission System," filed Jun. 16, 2001 by J. Elon Graves and Malcolm J. Northcott. All of the foregoing are incorporated herein by this reference.

In one embodiment, the iris imaging system of FIG. 2 is designed for use in airport hallways, customs checkpoints, public transportation stations, secure building lobbies, and the like. Standoff distances of up to at least 10 meters would enable the scanning of a large room or hallway to identify the occupants. For example, a device could be placed in the vicinity of the departure and/or arrival screen in an airport. The system would then be able to identify anyone attempting to read the screen contents.

For this specific design, the acquisition subsystem 100 has a field of view 135 of approximately 12 degrees, resulting in a capture volume 50 measuring approximately 2 m×2 m×2 m at a 10 m range (without scanning). The acquisition light source 110 is a light-emitting diode (LED) having a wavelength in the range of 750 to 980 nm. Shorter wavelengths give better sensor quantum efficiency, but wavelengths longer than approximately 890 nm are required for invisible operation. Longer wavelengths are also possible but require more expensive (not silicon) detectors. Extended incoherent light sources, particularly Light Emitting Diode (LED) sources are generally preferred. Laser sources are problematic due to eye safety considerations, but could be used with careful engineering. Gas discharge lamps or gas discharge flash lamps could also be used under some circumstances. Thermal sources such as tungsten lights, arc lamps, and high intensity discharge (HID) sources could also be used but would be inefficient due to the requirement for wavelength filtering. Eye safety is still a significant consideration, even using extended incoherent sources. Some traditional illumination sources (e.g., flash lamps) may exceed modern eye safety limits under some circumstances.

In this specific design, the illuminating wavelength used by the acquisition subsystem 100 is different than that used by the image capture subsystem 200, so mirror 119 can be wavelength-selective to separate the light for the acquisition subsystem 100 from that for the image capture subsystem. The acquisition camera 150 is an infrared enhanced monochrome TV camera with a resolution of approximately 720×500 pixels. The camera 150 operates at a 30 Hz frame rate.

With respect to the image capture subsystem 200, the resolution requirements drive in part the design of the iris imaging system 200. Consider a resolution requirement of 75 microns for the final, post processed image (e.g., measured as fullwidth half max of the aggregate point spread function, including effects of the optics, detector and post processing module 260). If the post processing module 260 is able to increase the resolution by 1.4×, then the required resolution for the image capture subsystem 200 is 105 microns. Assuming diffraction limited performance, the required aperture diameter d is given by d=λz/r, where z is the standoff distance and r is the required resolution. For example, assuming λ=0.85 µm, and z=10 m, the required aperture is 8.0 cm. Without post processing, the required aperture would be 11 cm. As another example, a 100 µm resolution can be achieved at a visible wavelength of 0.5 µm at a 10 m standoff distance with a diffraction limited 5 cm aperture (without post processing). A 1.4× increase in resolution due to post processing would yield an effective resolution of 70 µm for the same 5 cm aperture. However, infrared wavelengths are generally preferred for iris imaging due to the enhanced contrast observed at longer wavelengths. The enhanced contrast is particularly visible with brown eyes.

A distinction can be drawn between post processing based on deconvolution versus post processing based on superresolution. In deconvolution, the image is processed typically to increase the contrast of the image for spatial frequencies up to the cut off frequency of the optical system. The amount of contrast enhancement depends on signal to noise and the type of image degradation that has occurred. The improvement in resolution through deconvolution depends on the sampling rate (pixels/PSF FWHM) of the optical image. In one embodiment, the system is designed to have a FWHM of approximately 4 pixels at a standoff of 2 m. The maximum improvement in resolution due to deconvolution is approximately a factor of 3. However, to maintain Nyquist sampling to avoid introducing aliasing errors, the maximum resolution gain would be a factor of 2. This factor could be increased further with the addition of superresolution techniques.

In superresolution, the resolution can be increased beyond the cut-off frequency of the imaging system. In theory, superresolution is always possible, but signal to noise constraints typically restrict superresolution to resolution increased of no more than a factor of 2 or 3. Typically, superresolution is used with images that are nearly diffraction limited.

For both deconvolution and superresolution, oversampling (i.e. greater than Nyquist sampling) of the image is beneficial. In the case where aberrations in the optical system are sufficiently large, some spatial frequencies in the image may be zero due to a zero modulation transfer function (MTF). When zero MTF values are encountered, a good deconvolution algorithm will try to reconstruct the information at these zeros, thus taking on some of the characteristics of a super-resolution algorithm.

The use of post processing not only relaxes the resolution requirement for the image capture subsystem 200, but this in turn results in a larger depth of field. If the geometric image spread due to focus depth of field is set to be less than half of the diffraction limit, then the depth of field l is given by l=r²/λ. The 0.85 µm example yields a depth of field of approximately 7 mm without post processing and 14 mm with post processing. The 0.5 µm example yields a depth of field of approximately 2 cm without post processing and 4 cm with post processing. The actual extent of superresolution achievable is strongly dependent on the signal-to-noise ratio, which is in turn dependent on light level, among other factors. In situations where light level is constrained, a better choice may be to use a larger aperture, and use deconvolution to maximize the contrast of the resulting image. Depth of fields on the order of a few millimeters or a few centimeters makes focusing on moving objects difficult. Hence, it is advantageous for the adaptive optics loop to implement fast focus correction as well as fast tracking. With the adaptive optics augmented iris imaging system, images can be taken within a few milliseconds of identifying a target. Thus, the use of adaptive optics can increase the speed and accuracy of image capture for applications involving uncooperative targets.

Focus adjustment can also be achieved using other variations and approaches. For example, a variable focus lens or deformable mirror can be used to adjust the focus. Electromechanical lens position adjustment, movement of the camera 250 and use of a variable refractive index element are alternate ways to adjust focus. In addition, focus wavefront sensing can be based on image contrast measurements and dithering, or by use of a dedicated focus wavefront sensor, or by measuring the distance to the eye using time of flight of an optical or acoustic pulse.

Continuing with the specific example described above, the WFS light source 210 used in the iris imaging system 200 can be chosen to illuminate the eye so that the target individual is unaware of the process. LEDs having wavelengths in the range of 750 to 980 nm are generally preferred (and greater than approximately 890 nm for invisible operation), but other sources can be used as described above. Filling the telescope aperture with the illumination light as shown in FIG. 2 is advantageous, since it ensures that the pupil is fully illuminated by the eye reflection. The iris imaging light sources 248 are also preferably LEDs. Iris imaging standards currently specify wavelengths around the 850 nm range.

In this example, the WFS illuminating wavelength (used by the wavefront sensor 227) is also selected to be different from the illumination used to image the irises by camera 250. Hence, the beamsplitter 225 is dichroic to increase efficiency. However, these separations in wavelength are not required. The different beams can be separated using other techniques. For example, the iris imaging illumination and WFS illumination can be distinguished by time instead. The WFS LED 210 can be flashed synchronously with a WFS chopper (not shown in FIG. 2), and the iris imaging illumination 248 flashed to fill the dead time when the wavefront sensor 227 is not integrating signal. The iris imaging camera 250 preferably is a high quality monochrome imager. Due to the high speed tracking, this imager 250 can have a relatively small number of pixels, for instance a standard 640×480 video imager is convenient. For the iris imaging camera 250, high quality, high quantum efficiency and low signal to noise are relatively more important than resolution. The acquisition camera 150 will generally have a separate illumination system 110. If interference occurs between the acquisition illumination 110, the iris imaging illumination 248 and/or the fine tracking illumination 210, various techniques can be used to provide isolation, including for example techniques based on wavelength, polarization, temporal separation and/or angular or spatial separation.

Figure 3:
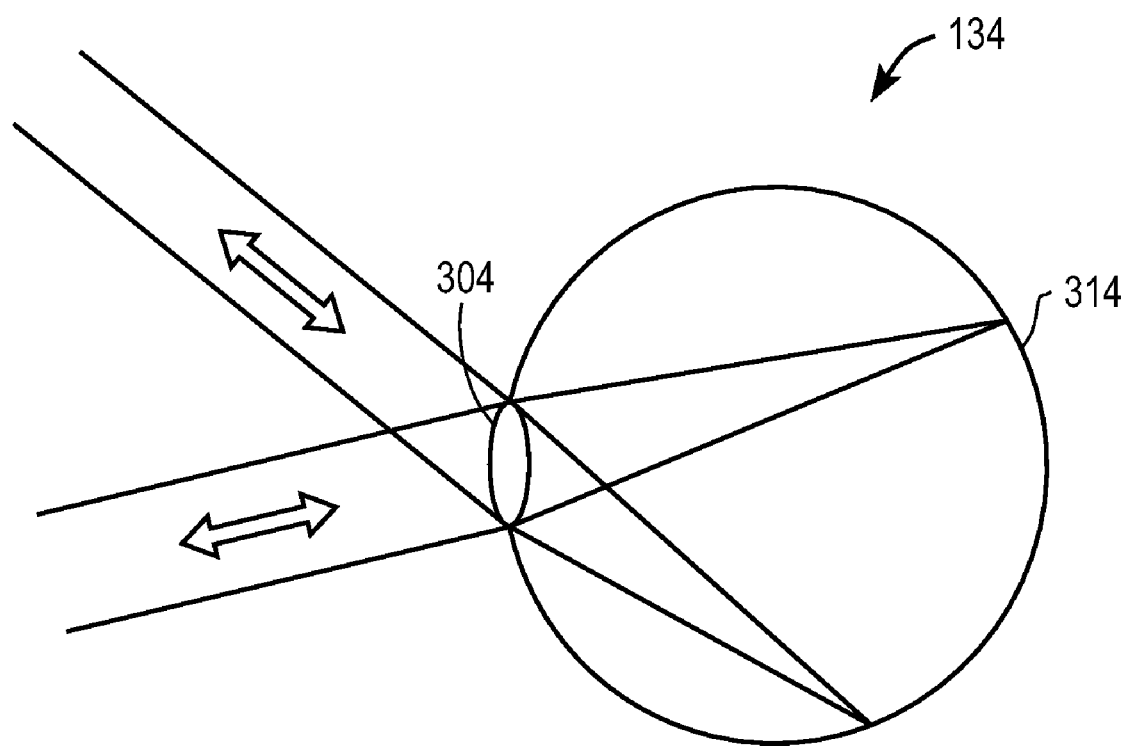
FIG. 3 is an illustration of retro-reflection from the eye.

The example of FIG. 2 is based on retro-reflection from the eye. FIG. 3 is an illustration of retro-reflection from the human eye. The intrinsic geometry of the eye causes it to act as a retro-reflector. Light that enters the eye lens 304 is focused onto the retina 314. Any light scattered by the retina back towards the lens 404 retraces its path out of the eye. Because the retina is in the focal plane of the eye lens, light is strongly directed in the backscatter direction. As FIG. 3 shows, light enters the eyeball through the pupil and reflects from the back curved surface of the retina 314. It is this back-reflection from the retina 314 that can be used to drive the fine tracking system in the image capture subsystem (e.g., the wavefront sensor in the adaptive optics loop). Also, the illustration of FIG. 3 shows that the illumination need not come from a face-on aspect to create a retro-reflection. Thus, the subject need not stare directly into the iris imaging camera for the acquisition and imaging system to work.

The following example demonstrates how retro-reflected light from an eye 234 can be used in closed loop operation of an adaptive optics system. A subject at a 10 m distance can be illuminated with 0.1 mW of power to the eye, which is well within the eye safety limit. In this example, the retro-reflected light is expected to be approximately $6.4 \times 10^{-13}$ W/cm². Assuming a 5 cm imaging lens is used to achieve a 100 micron resolution (before post processing), approximately $1.2 \times 10^{11}$ W is captured on the wavefront sensor. This corresponds to a photon flux of approximately $5 \times 10^7$ photons per second. In one embodiment, a low order adaptive optics system running at a relatively slow rate is used. For example, a 19 actuator adaptive optics system updated at 1 KHz, provides approximately 2500 photons per actuator per update. A CCD type detector with better than 50-electron read noise and 50% quantum efficiency will provide sufficient signal to noise ration for closed loop operation of the adaptive optics system. For comparison, better than 10-electron read noise and 90% quantum efficiency is routinely achieved for scientific grade CCD imaging. Thus, the retro-reflected light can be used to derive the feedback signal to support adaptive optics-assisted fine tracking and imaging.

Advantages of using the eye as a retro-reflector to drive the wavefront sensor include low cost and long range. The low cost is due to the ability to use an inexpensive silicon detector as the wavefront sensor and inexpensive LEDs as light sources. An adequate signal is achieved even at long ranges due to the strong directionality of the retro-reflection. However, the retinal retro-reflection does not appear as a point source, so higher dynamic range detectors are used to generate an accurate wavefront signal.

Figure 4:
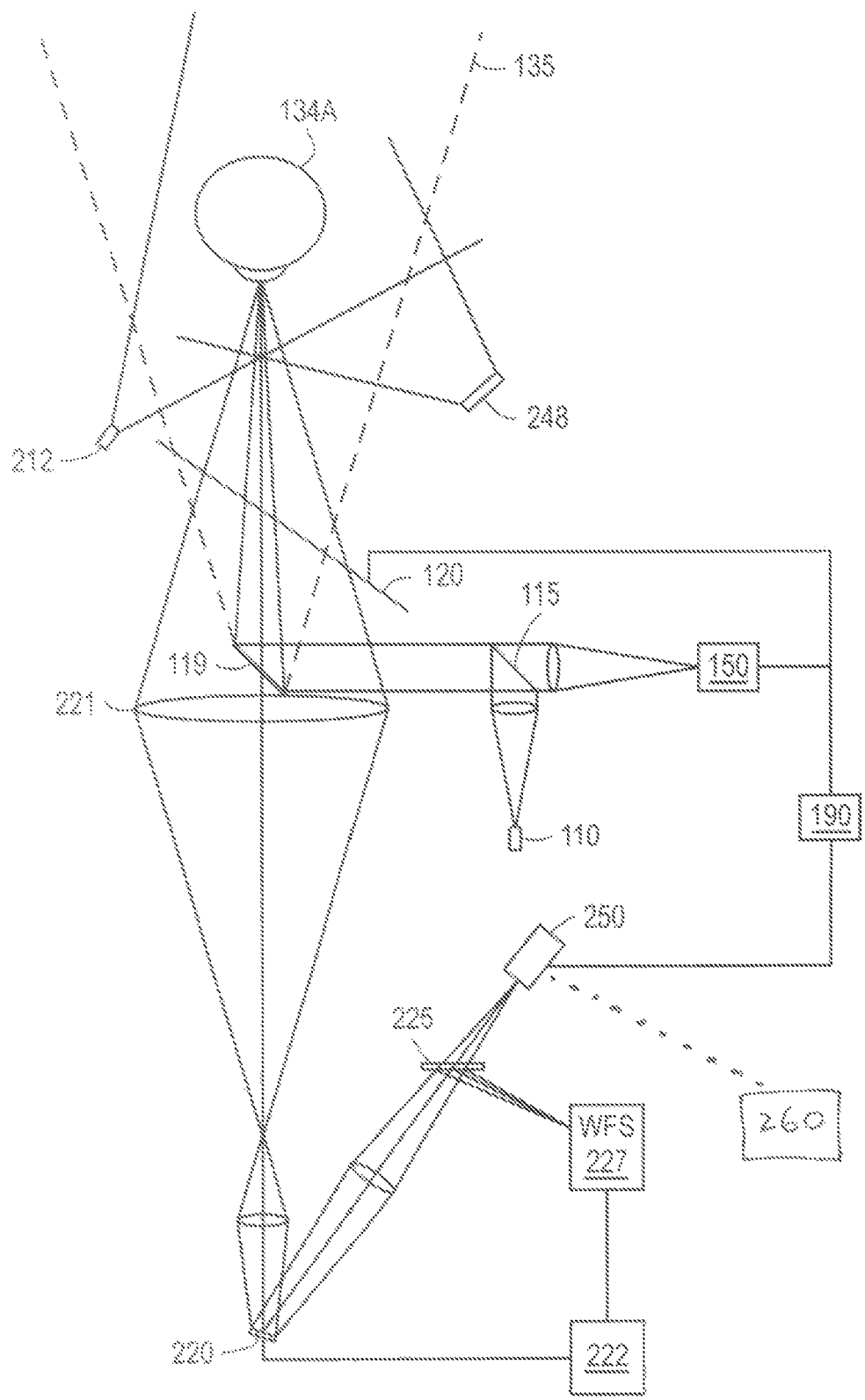
FIG. 4 is an illustration of another iris imaging system according to the present invention, based on glint from the eye.

In the example of FIG. 2, the reflection from the eye was a retinal retro-reflection. Alternatively, the front surface of the eye acts as a partial mirror with about 4% reflectivity. Reflections from this surface form a glint that can be used to steer the image capture subsystem 200, rather than steering based on the retro-reflection. For example, the system of FIG. 2 can be modified so that the light source 210 illuminates eye 134A, but the wavefront sensor 227 is driven by a glint reflection from the eye rather than a retro-reflection. Since glints can be produced by off-axis illumination, the light source 210 can be moved off-axis or even outside the telescope 221 for the image capture subsystem 200. In the example of FIG. 4, the light source 210 is replaced by an external light source 212. This source 212 is positioned at locations more like illuminators 248 but still produces a glint for telescope 221. In addition, the glint looks like a de-magnified image of the light source, so it tends to be more like a point source. A resulting advantage is that the size and shape of the glint is not a strong function of the distance to the subject.

One advantage of driving the wavefront sensor from the glint of the eyeball is that there is no limitation on distance over which glints from eyeballs can be used. Also, a point-like source does not require a wavefront sensor with a high dynamic range. However, glints return less light than retro-reflections from eyes, so more wavefront sensor sensitivity or a higher illumination flux may be required.

Image Post Processing

Turning now to the image post processing module 260, in FIGS. 2 and 4, an image post processing module 260 is coupled to an iris camera 250. As shown in FIG. 2, the post processing module 260 may be physically connected to the iris camera 250. Alternatively, as shown in FIG. 4, the post processing module 260 can be remotely located with respect to the camera 250 or other parts of the image capture subsystem 200 and configured to receive image data from the camera 250, for example wirelessly, or through a communication network. The image post processing module 260 receives iris images captured by the iris camera 250 and processes the iris images in order to enhance the quality of the images, such as by improving contrast, increasing resolution and/or reducing noise. The glints or specular reflections as well as the retinal reflection in the pupil region can be removed to prevent segmentation errors in the matching algorithms. More generally, the contrast between iris and scalera and the iris at the pupil can be enhanced to improve segmentation accuracies for matching algorithms.

Figure 5:
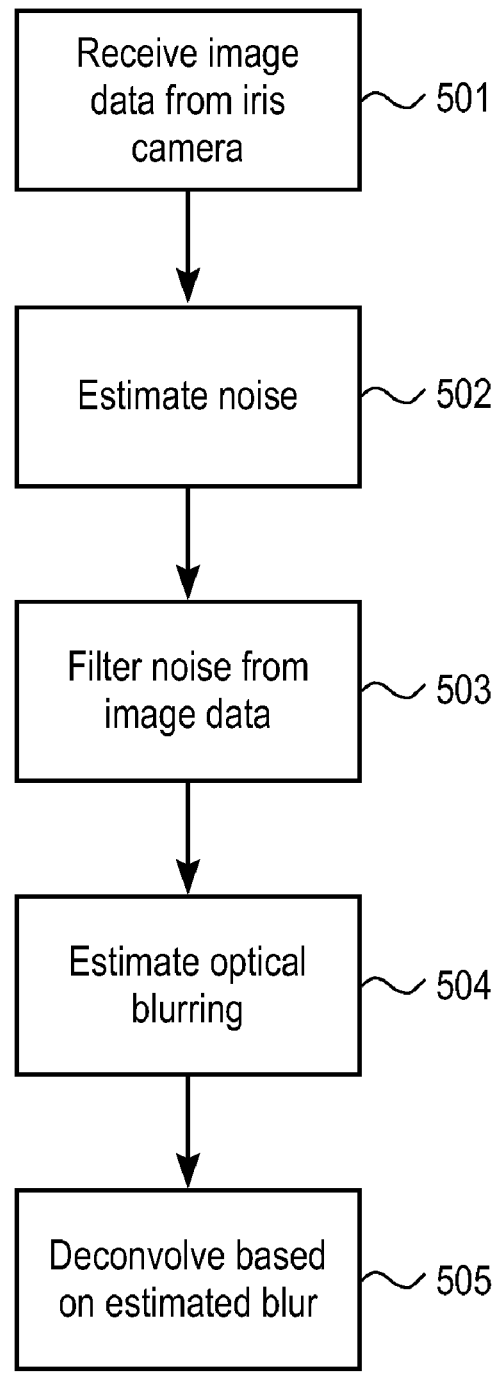
FIG. 5 is an illustration of an example method of post processing an iris image.

FIG. 5 is a flow chart of an example method 500 of improving an iris image obtained from an iris camera 250, according to one embodiment. The iris image is received 501 from the iris camera 250 by the image post processing module 260. In one implementation, the iris image is transferred to the post processing module 260 upon capture. In another implementation, image data may first be stored in a memory, for example, a memory present in the iris camera 250, and later transferred to the post processing module 260. A time-delayed transfer of data may be particularly advantageous in applications where stealth is desired and transmissions to a remote image post processing module may be vulnerable to interception at certain times. The transfer itself may be of raw image data or processed image data (portions of the post processing module 260 may be implemented at the camera). Compression, coding, encryption and other techniques may be used to enhance or secure the transfer. For clarity, the various steps have been represented by separate logical blocks in FIG. 5. In most implementations of deconvolution, noise filtering and deconvolution are inextricably linked in a single algorithm. However, an accurate estimate of the image noise content is essential for correct functioning of the algorithm.

Referring to example method 500, the captured image typically will be degraded by noise from various sources. In steps 502 and 503, the image post processing module 260 estimates 502 the noise in the iris image and then filters 503 the received iris image to remove the estimated noise. Various sources of noise can be present in the received image. For example, the iris camera 250 or other components may introduce electrical noise. As another example, low illumination of the iris may result in noise resulting from low photon counts. Aliasing noise which results from undersampling could be removed through high spatial frequency filtering, however a properly designed capture system with a PSF FWHM >2 pixels will not introduce aliasing noise. Noise may also be introduced by dark current, or thermally generated electron-hole pairs within the pixel substrate or on its surface.

In one embodiment, the noise is estimated from dark field or other experiments made to characterize the noise properties of the image capture subsystem 200. For example, as part of its calibration, the image capture subsystem 200 may be used to capture known images under controlled conditions (e.g., a series of uniform backgrounds at different illuminations) and these measurements can be used to estimate the noise characteristics, such as the noise spectral density. Alternately, the noise can be estimated based on modeling of the various noise sources within the image capture subsystem 200. Noise can also be estimated from a series of images of the same subject provided the conditions of the subject do not change significantly between images. An estimate of algorithm dependent matching errors can be made using a series of captured images. However, this noise is specific to the matching algorithm used and thus is harder to define. By estimating the noise and then effectively subtracting it out of the captured iris image, the image quality can be improved before additional post processing is undertaken. Alternatively or additionally, in other embodiments, other noise filtering steps known to those of skill in the art may be included at other points in the image post processing.

Step 503 and 504 address optical blurring. In step 503, the optical blurring introduces by the image capture subsystem 200 is estimated. This can then be used to sharpen the captured image via deconvolution or similar approaches.

In deconvolution-based approaches, the optical imaging process is modeled as G=F*H, where G is the Fourier transform of the captured blurred image (g), F is the Fourier transform of the unblurred image (f), and H is the Fourier transform of the blurring function (h). The captured image g is known. Therefore, if the blurring function h can be determined, various techniques can be applied to invert the convolution equation in order to solve for the sharp image f Blind deconvolution can also be used to estimate f and h, given g, and using image positivity constraints. If multiple images $g_1$, $g_2$, ... $g_n$ exist, differing only by differing blurring functions, $h_1, h_2, \ldots h_n$, then a better estimate off can typically be generated using a modified blind deconvolution algorithm.

For optical imaging systems, the blurring function h is often characterized by the point spread function (PSF). The PSF for an optical system can be estimated 503 in a number of different ways, including by theoretical calculation or based on experimental estimation. The accuracy of the estimated PSF influences the resolution of the post-processed image. In general, the better the approximation is, the more distortion can be removed from the image. In some cases, the PSF of the image capture subsystem is already known from previous calculations or experiments. A number of methods to approximate the PSF when it is not already known are described below. Note these methods can be used separately or in combination to estimate the PSF of the image capture subsystem.

In one embodiment, the light source 210, 212 used to drive the wavefront sensor 227 is used to estimate the PSF. If the light source 210, 212 produces a glint reflection from the eye, the glint will be point-like in nature. The image of the glint will be a direct measure of the PSF (recall that the PSF is the image produced by a point source). The glint image can be estimated by observing the appearance of the glint reflection in the captured image. The glint image is generally easy to locate because it is strong and point-like. This approach for directly estimating the PSF can generally be used with any light source that produces a point-like reflection. In one embodiment, wavelength filtering based on the wavelength of the light source can be used to further identify and separate the glint image from the rest of the iris image.

In a different approach, the PSF can be estimated during a calibration stage, rather than tracking glints from live subjects. For example, actual point sources can be located at various positions within the capture volume and a database of estimated PSFs assembled based on imaging these point sources. Alternately, the PSF can be derived from measurements of spatial resolution charts. In yet another approach, the PSF can be directly measured by test equipment designed for this purpose (e.g., equipment that measures wavefront quality) or can be estimated based on the paper design of the optical system. The PSF may also be estimated from the image of a known object, by a process similar to deconvolution. The PSF may also be estimated by combining information from a series of line spread functions using the Radon transform or similar technique. Line spread functions may be estimated from the edge of the pupil image or from other sharp boundaries in the image.

Regardless of how the PSF is estimated 504, in step 505, deconvolution is applied to the captured iris image in order to deblur the image. Various deconvolution algorithms can be used. In one embodiment, the Richardson-Lucy deconvolution algorithm is used. Examples of other widely used algorithms include maximum entropy deconvolution described in Frieden, B. R., 1972, J. Opt. Soc. Am. 63, 511, and Gull, S. F. & Daniell, G. J., 1978, Nature, 272, 686; the Wiener Filtering method described in Press et al., 1986, *The Art of scientific Computing*, Cambridge Univ. Press, the CLEAN method described in Hogbom, J. A., 1974, A&AS, 15, 417, and the Jansson Van Cittert deconvolution method described in Jansson, P. A., 1970, J. Opt Soc. Am., 60, 184. All of the foregoing are incorporated herein by reference in their entirety. Different deconvolution algorithms are based on different noise assumptions. In one embodiment, the deconvolution algorithm is selected dynamically based on the noise characteristics of the image. For example, one deconvolution algorithm may be used if the predominant noise is Gaussian whereas a different deconvolution algorithm may be used for Poisson noise. The application of the deconvolution algorithm to the iris image deblurs the image, thus improving the image quality (specifically, image resolution).

Method 500 is merely an example. Other post processing approaches will be apparent. For example, neither the noise reduction step 502-503 or the deconvolution step 504-505 is required. Each can be used without the other and/or in combination with other post processing techniques. The two can also be combined into a single step. For example, the Richardson-Lucy algorithm assumes a certain form of noise and then produces the optimal deconvolution given that noise. It achieves both deconvolution and noise compensation.

As another example, deconvolution 505 can be achieved without expressly estimating 504 the blurring function. This is commonly referred to as blind deconvolution. Examples of blind deconvolution algorithms include those described in Jefferies, S. M, Christou, J. C., 1993, ApJ, 415, 862, and Blind Deconvolution using Lucy algorithm described by Tsumuraya, F., Miura, N., Baba, N., 1994, A&A 282, 699, which are both incorporated herein by reference in their entirety. For purposes of iris identification with the iris capture system 200, the improvement from blind deconvolution is similar to that achieved by deconvolution using a given PSF, for example, a factor of 2 to 3. This is limited by the original sampling and signal to noise ratio of the image.

As another example, alternative or additional post processing of the iris image can be performed by processing a series of iris images. In one approach, a series of iris images are captured in rapid succession. Improved performance can be achieved by processing several images of the same object with different noise and possibly different point spread functions according to the method 500 described above. In one embodiment, individual images of the same subject can be deconvolved and noise filtered. These images can then be stacked or overlaid to improve the signal to noise ratio of the resulting composite image.

In another embodiment, the image resolution can be enhanced through use of super-resolution techniques used with a set of images of the same subject. Super-resolution is a technique to use multiple frames of the same object to achieve a higher resolution image. In one embodiment, multiple images are taken of an iris in quick succession, with the goal of obtaining several image frames of an iris, where the iris is shifted by a fraction of a pixel from one frame to the next. A super-resolution algorithm produces a higher resolution image that contains the information in the multiple, lower resolution original images. In one embodiment, super-resolution is used with images obtained through short exposures, because long exposures may result in a blurred image from subtle movements of the subject (i.e., motion blurring).

If desired, the multiple images of an iris that are obtained from the imaging system can be transformed by the image post processing module using conformal distortion techniques. Conformal distortion techniques can be used to transform images of an iris taken at various "glance" angles to images with a face-on aspect. Other non-conformal distortions can also be used, but must generally be one to one or bijective. In one embodiment, retro-reflection from the retina is used to determine the degree of geometric transformation needed. At a face-on aspect, the retinal retro-reflection is approximately circular. As the glance angle increases, the retinal retro-reflection appears increasingly elliptical in shape. The measurement of this effect can be used to determine the correction to apply to the image, using conformal distortion techniques, in order to produce an image of an iris at a face-on aspect. In one approach, the different images are geometrically stretched or shrunk so that the retinal retro-reflections in the different images all have the same aspect ratio. Then, the techniques described above for improving image quality by using multiple images of the same subject can be applied to the set of images.

The image post processing module 260 can also correct for non-convolutional effects. For example, if the image capture subsystem introduces pincushion or barrel distortion, the image post processing module 260 can apply a coordinate transform to the captured iris image in order to undo the effects of the distortion.

The present invention has been described in particular detail with respect to several possible embodiments. Those of skill in the art will appreciate that the invention may be practiced in other embodiments. First, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. For example, the fine tracking system within the image capture subsystem may use a deformable mirror to steer the camera from eye to eye, but the deformable mirror may be driven by feedback other than from a wavefront sensor. For example LIDAR, radar and other range finding technologies, image parallax or image contrast measurements and pattern recognition can be used to drive the deformable mirror. Therefore, the scope of the invention should be determined by the appended claims and their legal equivalents.

What is claimed is:

1. A method for processing an image of an iris of an eye, comprising:
   illuminating the eye with light;
   steering a camera to the eye based on a reflection of the illuminating light from the eye;
   the camera capturing an image of the iris of the eye; and
   post processing, using an image post processing module, the captured iris image to produce a post processed iris image with a resolution of 200 microns or better and sufficient resolution for biometric identification.

2. The method of claim 1 wherein the step of post processing comprises applying deconvolution to the captured iris image.

3. The method of claim 2 wherein the step of applying deconvolution comprises:
   estimating a point spread function from a glint reflection from the eye; and
   applying deconvolution based on the estimated point spread function.

4. The method of claim 2 wherein the step of applying deconvolution comprises applying blind deconvolution to the captured iris image.

5. The method of claim 1 wherein the step of post processing comprises noise filtering the captured iris image.

6. The method of claim 1 wherein the step of post processing comprises applying a super-resolution algorithm to two or more captured iris images.

7. The method of claim 1 wherein the step of post processing comprises overlaying two or more captured iris images.

8. The method of claim 1 wherein the reflection from the eye is a retro-reflection from the eye.

9. The method of claim 1 wherein the reflection from the eye is a glint reflection from the eye.

10. The method of claim 1 wherein the step of steering the camera to the eye comprises using an adaptive optics loop based on the light reflected from the eye to steer the camera to the eye.

11. The method of claim 1 wherein the post processed iris image has a resolution that is at least 1.2 times better than that of the captured iris image.

12. The method of claim 1 wherein the camera can be steered to cover a capture volume of at least 1 cubic meter.

13. The method of claim 1 wherein the camera can capture iris images at a standoff of at least 1 m.

14. The method of claim 1 wherein the captured iris image has insufficient resolution for biometric identification.

15. A method for processing an image of an iris of an eye, comprising:
   capturing an image of the iris of the eye;
   estimating, using an image post processing module, a point spread function from a reflection from the eye; and
   applying deconvolution, using the image post processing module, to the captured iris image based on the estimated point spread function to produce a post processed iris image a resolution of 200 microns or better and sufficient resolution for biometric identification.

16. The method of claim 15 further comprising noise filtering the captured iris image.

17. The method of claim 15 wherein the reflection from the eye is a retro-reflection from the eye.

18. The method of claim 15 wherein the reflection from the eye is a glint reflection from the eye.

19. The method of claim 15 further comprising:
illuminating the eye with light;
wherein the step of capturing an image of the iris comprises capturing the image of the iris illuminated by the illuminating light; and
wherein the step of estimating a point spread function from a reflection from the eye comprises estimating a point spread function from a reflection of the illuminating light from the eye.

20. The method of claim 15 further comprising:
illuminating the eye with light;
steering a camera to the eye based on a reflection of the illuminating light from the eye; and
wherein the step of estimating a point spread function from a reflection from the eye comprises estimating a point spread function from a reflection of the illuminating light from the eye.

21. The method of claim 15 wherein the post processed iris image has a resolution that is at least 1.2 times better than that of the captured iris image.

22. The method of claim 15 wherein the step of capturing an image of the iris occurs over a capture volume of at least 1 cubic meter.

23. The method of claim 15 wherein the step of capturing an image of the iris occurs at a standoff of at least 1 m.

24. The method of claim 15 wherein the captured iris image has insufficient resolution for biometric identification.

25. An iris imaging system for processing an image of an iris of an eye comprising:
an image capture subsystem comprising:
a light source for illuminating the eye with light;
a camera for capturing an image of the iris of the eye; and
a fine tracking system for steering a camera to the eye based on a reflection of the illuminating light from the eye; and
an image post processing module communicatively coupled to the image capture subsystem, for post processing the captured iris image to produce a post processed iris image with a resolution of 200 microns or better and sufficient resolution for biometric identification.

26. The iris imaging system of claim 25 wherein the image post processing module applies deconvolution to the captured iris image.

27. The iris imaging system of claim 25 wherein the reflection from the eye is a retro-reflection from the eye.

28. The iris imaging system of claim 25 wherein the reflection from the eye is a glint reflection from the eye.

29. The iris imaging system of claim 25 wherein fine tracking system includes an adaptive optics loop.

30. The iris imaging system of claim 25 wherein the captured iris image has insufficient resolution for biometric identification.

31. A iris imaging system for processing an image of an iris of an eye comprising:
an image capture subsystem for capturing an image of the iris of the eye; and
an image post processing module communicatively coupled to the image capture subsystem, for estimating a point spread function from a reflection from the eye and further for applying deconvolution to the captured iris image based on the estimated point spread function to produce a post processed iris image with a resolution of 200 microns or better and sufficient resolution for biometric identification.

32. The iris imaging system of claim 31 wherein the reflection from the eye is a retro-reflection from the eye.

33. The iris imaging system of claim 31 wherein the reflection from the eye is a glint reflection from the eye.

34. The iris imaging system of claim 31 wherein the light producing the reflection from the eye also illuminates the iris for capture by the image capture subsystem.

35. The iris imaging system of claim 31 wherein the light producing the reflection from the eye is also used to steer the image capture subsystem to the eye.

36. The iris imaging system of claim 31 wherein the captured iris image has insufficient resolution for biometric identification.

37. A method for processing an image of an iris of an eye, comprising:
illuminating the eye with light;
steering a camera to the eye based on a reflection of the illuminating light from the eye;
the camera capturing an image of the iris of the eye; and
post processing, using an image post processing module, the captured iris image to produce a post processed iris image with a resolution that is at least 1.2 times better than that of the captured iris image and with sufficient resolution for biometric identification.

38. The method of claim 37 wherein the step of post processing comprises applying deconvolution to the captured iris image.

39. The method of claim 38 wherein the step of applying deconvolution comprises:
estimating a point spread function from a glint reflection from the eye; and
applying deconvolution based on the estimated point spread function.

40. The method of claim 38 wherein the step of applying deconvolution comprises applying blind deconvolution to the captured iris image.

41. The method of claim 37 wherein the step of post processing comprises noise filtering the captured iris image.

42. The method of claim 37 wherein the step of post processing comprises applying a super-resolution algorithm to two or more captured iris images.

43. The method of claim 37 wherein the step of post processing comprises overlaying two or more captured iris images.

44. The method of claim 37 wherein the reflection from the eye is a retro-reflection from the eye.

45. The method of claim 37 wherein the reflection from the eye is a glint reflection from the eye.

46. The method of claim 37 wherein the step of steering the camera to the eye comprises using an adaptive optics loop based on the light reflected from the eye to steer the camera to the eye.

47. The method of claim 37 wherein the post processed iris image has a resolution of 200 microns or better.

48. The method of claim 37 wherein the camera can be steered to cover a capture volume of at least 1 cubic meter.

49. The method of claim 37 wherein the camera can capture iris images at a standoff of at least 1 m.

50. The method of claim 37 wherein the captured iris image has insufficient resolution for biometric identification.

51. A method for processing an image of an iris of an eye, comprising:
capturing an image of the iris of the eye;
estimating, using an image post processing module, a point spread function from a reflection from the eye; and
applying deconvolution, using the image post processing module, to the captured iris image based on the estimated point spread function to produce a post processed iris image with a resolution that is at least 1.2 times better than that of the captured iris image and with sufficient resolution for biometric identification.

52. The method of claim 51 further comprising noise filtering the captured iris image.

53. The method of claim 51 wherein the reflection from the eye is a retro-reflection from the eye.

54. The method of claim 51 wherein the reflection from the eye is a glint reflection from the eye.

55. The method of claim 51 further comprising:
illuminating the eye with light;
wherein the step of capturing an image of the iris comprises capturing the image of the iris illuminated by the illuminating light; and
wherein the step of estimating a point spread function from a reflection from the eye comprises estimating a point spread function from a reflection of the illuminating light from the eye.

56. The method of claim 51 further comprising:
illuminating the eye with light;
steering a camera to the eye based on a reflection of the illuminating light from the eye; and
wherein the step of estimating a point spread function from a reflection from the eye comprises estimating a point spread function from a reflection of the illuminating light from the eye.

57. The method of claim 51 wherein the post processed iris image has a resolution of 200 microns or better.

58. The method of claim 51 wherein the step of capturing an image of the iris occurs over a capture volume of at least 1 cubic meter.

59. The method of claim 51 wherein the step of capturing an image of the iris occurs at a standoff of at least 1 m.

60. The method of claim 51 wherein the captured iris image has insufficient resolution for biometric identification.

61. An iris imaging system for processing an image of an iris of an eye comprising:
an image capture subsystem comprising:
a light source for illuminating the eye with light;
a camera for capturing an image of the iris of the eye; and
a fine tracking system for steering a camera to the eye based on a reflection of the illuminating light from the eye; and
an image post processing module communicatively coupled to the image capture subsystem, for post processing the captured iris image to produce a post processed iris image with a resolution that is at least 1.2 times better than that of the captured iris image and with sufficient resolution for biometric identification.

62. The iris imaging system of claim 61 wherein the image post processing module applies deconvolution to the captured iris image.

63. The iris imaging system of claim 61 wherein the reflection from the eye is a retro-reflection from the eye.

64. The iris imaging system of claim 61 wherein the reflection from the eye is a glint reflection from the eye.

65. The iris imaging system of claim 61 wherein fine tracking system includes an adaptive optics loop.

66. The iris imaging system of claim 61 wherein the captured iris image has insufficient resolution for biometric identification.

67. A iris imaging system for processing an image of an iris of an eye comprising:
an image capture subsystem for capturing an image of the iris of the eye; and
an image post processing module communicatively coupled to the image capture subsystem, for estimating a point spread function from a reflection from the eye and further for applying deconvolution to the captured iris image based on the estimated point spread function to produce a post processed iris image with a resolution that is at least 1.2 times better than that of the captured iris image and with sufficient resolution for biometric identification.

68. The iris imaging system of claim 67 wherein the reflection from the eye is a retro-reflection from the eye.

69. The iris imaging system of claim 67 wherein the reflection from the eye is a glint reflection from the eye.

70. The iris imaging system of claim 67 wherein the light producing the reflection from the eye also illuminates the iris for capture by the image capture subsystem.

71. The iris imaging system of claim 67 wherein the light producing the reflection from the eye is also used to steer the image capture subsystem to the eye.

72. The iris imaging system of claim 67 wherein the captured iris image has insufficient resolution for biometric identification.

73. A method for processing an image of an iris of an eye, comprising:
illuminating the eye with light;
steering a camera to the eye based on a reflection of the illuminating light from the eye, wherein the camera can be steered to cover a capture volume of at least 1 cubic meter;
the camera capturing an image of the iris of the eye; and
post processing, using an image post processing module, the captured iris image to produce a post processed iris image with sufficient resolution for biometric identification.

74. The method of claim 73 wherein the step of post processing comprises applying deconvolution to the captured iris image.

75. The method of claim 74 wherein the step of applying deconvolution comprises:
estimating a point spread function from a glint reflection from the eye; and
applying deconvolution based on the estimated point spread function.

76. The method of claim 74 wherein the step of applying deconvolution comprises applying blind deconvolution to the captured iris image.

77. The method of claim 73 wherein the step of post processing comprises noise filtering the captured iris image.

78. The method of claim 73 wherein the step of post processing comprises applying a super-resolution algorithm to two or more captured iris images.

79. The method of claim 73 wherein the step of post processing comprises overlaying two or more captured iris images.

80. The method of claim 73 wherein the reflection from the eye is a retro-reflection from the eye.

81. The method of claim 73 wherein the reflection from the eye is a glint reflection from the eye.

82. The method of claim 73 wherein the step of steering the camera to the eye comprises using an adaptive optics loop based on the light reflected from the eye to steer the camera to the eye.

83. The method of claim 73 wherein the post processed iris image has a resolution that is at least 1.2 times better than that of the captured iris image.

84. The method of claim 73 wherein the post processed iris image has a resolution of 200 microns or better.

85. The method of claim 73 wherein the camera can capture iris images at a standoff of at least 1 m.

86. The method of claim 73 wherein the captured iris image has insufficient resolution for biometric identification.

87. A method for processing an image of an iris of an eye, comprising:
capturing an image of the iris of the eye, wherein capturing the image of the iris occurs over a capture volume of at least 1 cubic meter;
estimating, using an image post processing module, a point spread function from a reflection from the eye; and
applying deconvolution, using the image post processing module, to the captured iris image based on the estimated point spread function to produce a post processed iris image sufficient resolution for biometric identification.

88. The method of claim 87 further comprising noise filtering the captured iris image.

89. The method of claim 87 wherein the reflection from the eye is a retro-reflection from the eye.

90. The method of claim 87 wherein the reflection from the eye is a glint reflection from the eye.

91. The method of claim 87 further comprising:
illuminating the eye with light;
wherein the step of capturing an image of the iris comprises capturing the image of the iris illuminated by the illuminating light; and
wherein the step of estimating a point spread function from a reflection from the eye comprises estimating a point spread function from a reflection of the illuminating light from the eye.

92. The method of claim 87 further comprising:
illuminating the eye with light;
steering a camera to the eye based on a reflection of the illuminating light from the eye; and
wherein the step of estimating a point spread function from a reflection from the eye comprises estimating a point spread function from a reflection of the illuminating light from the eye.

93. The method of claim 87 wherein the post processed iris image has a resolution that is at least 1.2 times better than that of the captured iris image.

94. The method of claim 87 wherein the post processed iris image has a resolution of 200 microns or better.

95. The method of claim 87 wherein the step of capturing an image of the iris occurs at a standoff of at least 1 m.

96. The method of claim 87 wherein the captured iris image has insufficient resolution for biometric identification.

97. An iris imaging system for processing an image of an iris of an eye comprising:
an image capture subsystem comprising:
a light source for illuminating the eye with light;
a camera for capturing an image of the iris of the eye, wherein the camera can be steered to cover a capture volume of at least 1 cubic meter; and
a fine tracking system for steering a camera to the eye based on a reflection of the illuminating light from the eye; and
an image post processing module communicatively coupled to the image capture subsystem, for post processing the captured iris image to produce a post processed iris image with sufficient resolution for biometric identification.

98. The iris imaging system of claim 97 wherein the image post processing module applies deconvolution to the captured iris image.

99. The iris imaging system of claim 97 wherein the reflection from the eye is a retro-reflection from the eye.

100. The iris imaging system of claim 97 wherein the reflection from the eye is a glint reflection from the eye.

101. The iris imaging system of claim 97 wherein fine tracking system includes an adaptive optics loop.

102. The iris imaging system of claim 97 wherein the captured iris image has insufficient resolution for biometric identification.

103. A iris imaging system for processing an image of an iris of an eye comprising:
an image capture subsystem for capturing an image of the iris of the eye, wherein capturing the image of the iris occurs over a capture volume of at least 1 cubic meter; and
an image post processing module communicatively coupled to the image capture subsystem, for estimating a point spread function from a reflection from the eye and further for applying deconvolution to the captured iris image based on the estimated point spread function to produce a post processed iris image with sufficient resolution for biometric identification.

104. The iris imaging system of claim 103 wherein the reflection from the eye is a retro-reflection from the eye.

105. The iris imaging system of claim 103 wherein the reflection from the eye is a glint reflection from the eye.

106. The iris imaging system of claim 103 wherein the light producing the reflection from the eye also illuminates the iris for capture by the image capture subsystem.

107. The iris imaging system of claim 103 wherein the light producing the reflection from the eye is also used to steer the image capture subsystem to the eye.

108. The iris imaging system of claim 103 wherein the captured iris image has insufficient resolution for biometric identification.

* * * * *